United States Patent
Gadhe et al.

(10) Patent No.: US 9,919,318 B2
(45) Date of Patent: Mar. 20, 2018

(54) PROCESS FOR PREPARATION OF HIGH FLASH POINT FROTHING AGENT

(71) Applicant: Godavari Blorefineries Limited, Mumbai (IN)

(72) Inventors: Ravindra Gadhe, Mumbai (IN); Shanul Pagar, Mumbai (IN); Sangeeta Srivastava, Mumbai (IN)

(73) Assignee: Godavari Biorefineries Limited, Mumbai (IN)

( * ) Notice: Subject to any disclaimer, the term of this patent is extended or adjusted under 35 U.S.C. 154(b) by 0 days.

(21) Appl. No.: 15/129,722

(22) PCT Filed: Mar. 27, 2015

(86) PCT No.: PCT/IB2015/052270
§ 371 (c)(1),
(2) Date: Sep. 27, 2016

(87) PCT Pub. No.: WO2015/145394
PCT Pub. Date: Oct. 1, 2015

(65) Prior Publication Data
US 2017/0173595 A1    Jun. 22, 2017

(30) Foreign Application Priority Data

Mar. 28, 2014  (IN) .......................... 837/MUM/2014

(51) Int. Cl.
*B03D 1/008*   (2006.01)
*C07C 41/42*   (2006.01)
*C07C 41/06*   (2006.01)

(52) U.S. Cl.
CPC .............. *B03D 1/008* (2013.01); *C07C 41/06* (2013.01); *C07C 41/42* (2013.01); *B03D 2201/04* (2013.01)

(58) Field of Classification Search
CPC .... B03D 1/008; B03D 2201/04; C07C 41/42; C07C 41/06; C07C 41/54; C07C 41/56
See application file for complete search history.

(56) References Cited

U.S. PATENT DOCUMENTS

| | | |
|---|---|---|
| 2,212,894 A | 8/1940 | Allen |
| 2,561,251 A | 7/1951 | Van Aardt |
| 2,800,513 A | 7/1957 | Hall et al. |
| 2006/0239876 A1 | 10/2006 | Leeming et al. |

FOREIGN PATENT DOCUMENTS

GB            697905           9/1953

OTHER PUBLICATIONS

International Search Reportand Written Opinion from the USPTO, acting as the International Searching Authority, for international application PCT/IB2015/052270 dated Jul. 22, 2015.

*Primary Examiner* — Rosalynd A Keys
(74) *Attorney, Agent, or Firm* — McCarter & English, LLP

(57) ABSTRACT

The present invention discloses a process for preparing high flash point frothing agent by treating an aldehyde with an alcohol in the presence of an acid catalyst at elevated temperature and further adding a carbonate salt to obtain the frothing agent and polymer.

10 Claims, No Drawings

US 9,919,318 B2

PROCESS FOR PREPARATION OF HIGH FLASH POINT FROTHING AGENT

CROSS-REFERENCE TO RELATED APPLICATIONS

This application is the National Stage entry under 35 U.S.C. § 371 International Application No. PCT/IB2015/052270 filed on Mar. 27, 2015,published on Oct. 1, 2015 under publication number WO 2015/145394 A1, which claims the benefit of priority under 35 U.S.C. § 119 of Indian patent application number 837/MUM/2014 filed Mar. 28, 2014.

FIELD OF THE INVENTION

The present invention relates to a process for producing frothing agents having high flash point.

BACKGROUND OF THE INVENTION

Froth flotation is a commonly employed process for physical separation of minerals from its ore. In a flotation process, the ore is crushed and wet ground to obtain a pulp. The pulp is then aerated to produce froth at the surface. A frothing agent is added to the mixture to assist in separating valuable components from the undesired portions of the mixture in subsequent flotation steps. The basic function of the frother is to produce a swarm of air bubbles, which remain sufficiently stable for the hydrophobic mineral particles to be captured by them. The hydrophobic materials are buoyed by the bubbles bringing them to float on the surface.

The hydrophobic materials -bearing froth is collected and further processed to obtain the desired products. That portion of the ore which is not carried over with the froth is usually not further processed for extraction of mineral values there from.

While a large number of compounds have foam or froth producing properties, the frothers most widely used in commercial froth flotation operations are monohydroxylated compounds such as alcohols, pine oils, cresols and alkyl ethers of polypropylene glycols as well as dihydroxylates such as polypropylene glycols. Other effective frothers used commercially are alkyl ethers of polypropylene glycol, especially the methyl ether and the polypropylene glycols. As disclosed in U.S. Ser. No. 06/923,523 and Surface chemistry of Froth floatation by S.R.Rao.

Overall, methyl isobutyl carbinol (MIBC) is the most commonly used frother. However, there have been environmental concerns with regard to MIBC's low flash-point temperature and high vaporization rate that produces an unpleasant odor in warmer climates. As stated in Froth floatation—A century of innovation.

Therefore, there is a need for an alternative process to produce frothing agents having high flash point.

SUMMARY OF THE INVENTION

The present invention discloses a process for preparing a frothing agent having high flash point by treating an aldehyde with an alcohol in the presence of an acid catalyst at elevated temperature and further adding a carbonate salt for neutralization of the acid catalyst to obtain the frothing agent and polymer.

DESCRIPTION OF THE INVENTION

In one embodiment of the present invention, the process for preparing a high flash point frothing agent comprises of:
treating an aldehyde with an alcohol in the presence of an acid catalyst at an elevated temperature to form a mixture; and
adding a carbonate salt to the mixture for neutralizing the acid catalyst to obtain frothing agent and polymer.

The temperature of the reaction is maintained in the range of 75° C. to 80° C. The reactants are heated for 3-4 hours after addition of the carbonate salt.

The unreacted alcohol that is present in the mixture after the reaction is distilled out and optionally is recycled back to the step of treating aldehyde with an alcohol in the presence of the acid catalyst. The low boiling impurities present in the mixture is also removed by distillation.

The carbonate salt added to neutralize the acid catalyst forms a salt with the acid catalyst and can be easily removed.

The mixture comprising crude frothing agent is distilled out by fractional distillation to obtain pure high flash point frothing agent. The flash point of the frothing agent obtained by the process of the present invention is above 60° C.

In an embodiment of the present invention a process for preparing high flash point frothing agent comprises of treating an aldehyde and an alcohol in the presence of an acid catalyst at an elevated temperature in the range of 75° C.-80° C. A carbonate salt is added to the mixture for neutralizing the acid catalyst to form frothing agent and a polymer mixture.

In one embodiment of the present invention, the process for preparing a high flash point frothing agent comprises of:
treating an aldehyde with an alcohol in the presence of an acid catalyst to form a mixture;
heating the mixture at an elevated temperature;
adding a carbonate salt for neutralising the acid catalyst to obtain frothing agent and polymer mixture;
recovering the unreacted alcohol and recycling it to the first step of treating an aldehyde with an alcohol; and
distilling the frothing agent and polymer mixture by fractional distillation to obtain pure frothing agent.

The unreacted alcohol is recovered by distillation.

The temperature is maintained in the range of 75° C. to 80° C. After adding the carbonate salt, the reaction is carried out for 3-4 hours.

The aldehyde used in the process is preferably an α-β unsaturated aldehyde. The carbon atom in the aldehyde varies from $C_4$ to $C_{10}$. Examples include but are not limited to crotonaldehyde, 2-ethyl hexenal, 2-ethyl crotonaldehyde, 2,4-hexadienal, 2,4,6 octatrinal or mixture thereof. The aldehyde is preferably crotonaldehyde.

In one embodiment of the present invention a mixture of aldehyde having $C_4$-$C_{10}$ carbon atoms is used.

In an embodiment of the present invention a mixture of aldehyde having $C_4$-$C_8$ carbon atoms is used.

The alcohol used in the process is an aliphatic alcohol having $C_3$ to $C_{10}$ carbon atoms. Examples include but are not limited to methyl alcohol, ethyl alchol, propyl alcohol, butyl alchol, hexanol, octanol or mixture thereof. The alcohol used is preferably ethyl alcohol.

The molar ratios of aldehyde and alcohol used for the reation are in the range of 1:6 to 1:20, preferably 1:10.

The acid catalyst used in the process includes but is not limited to hydrochloric acid, sulfuric acid, paratoluene sulfonic acid, super acid, cation exchange resin such as Indion-130 or mixture thereof. The acid catalyst is preferably paratoluene sulphonic acid.

The carbonate salt used in the process is sodium carbonate, calcium carbonate, magnesium carbonate or mixture thereof.

In a preferred embodiment of the present invention, a process for preparing high flash point 1,1,3-triethoxy butane comprises of:

treating crotonaldehyde with ethyl alcohol in the presence of paratoluene sulfonic acid to form a mixture;

heating the mixture at a temperature of 75° C.-80° C.;

adding sodium carbonate for neutralizing paratoluene sulfonic acid to obtain crude 1,1,3-triethoxy butane and polymer; and distilling 1,1,3-triethoxy butane and polymer mixture by fractional distillation to obtain pure 1,1,3-triethoxy butane.

The process of the present invention improves the yield and high flash point of the frother. The frothing agents obtained by the process of the present invention have a high flash point of above 60° C., which makes the handling of such frothing agents much easier. The major disadvantage of low flash point frothing agents is their transportation and storage. Frothing agents having flash point below 60° C. is considered as dangerous good for air, sea and road transportation which requires special handling and care. Considering end user point of view, the storage of material with low flashpoint is always a risk with respect to working environment and fire hazards.

The high heating temperature selected in the present process forms a product and polymer. The presence of a polymer results in a higher flash point of the product. Before recovery of unreacted alcohol, the catalyst is neutralized using a carbonate salt to form salt which is easily separated by filtration. The crude product having low boiling impurities which affect the flash point are removed by fractional distillation under reduced pressure which causes further increase in the flash point. The purity of the final high flash point frothing agent is 92-95%. The selectivity of product on the aldehyde used is 83%. The high flash point contributes to efficient flotation over a wide range of operating temperatures. The unreacted alcohol is recycled back to the process step and this avoids the wastage of the unreacted alcohol.

EXAMPLES

The following examples illustrate the invention but are not limiting thereof.

Example 1

Process for Preparing 1,1,1 Triethoxy Butane 70 gms of crotonaldehyde, 920 gms of ethyl alcohol was charged in to a round bottom flask, which was attached to a reflux condensor. 10 gms of paratoulene sulphonic acid was added to the round bottom flask and the contents were heated at a temperature of 78° C. for 7 hours. After heating, the reaction mass was cooled and was neutralized by adding 4 gms of sodium carbonate at room temperature to obtain 1,1,1 triethoxy butane and polymer. The reaction mass was distilled at atmospheric pressure to recover ethyl alcohol and remove low boiling impurities. The recovered ethyl alcohol was recycled back to the round bottom flask containing crotonaldehyde, ethyl alcohol and para toluene sulphonic acid. The remaining product obtained was 165 gms of 1,1,1 triethoxy butane. The flash point of 1,1,1 triethoxy butane was 64° C.

1,1,1 triethoxy butane having high flash point of 64° C. was tested under standard conditions for its frothing properties.

Lead-Zinc Ore

Lead-Zinc ore was ground to size below 100 μm and used for all the flotation tests. The flotation tests were carried out in a Denver D-12 sub-aeration flotation machine with 2 liter capacity cell. Flotation tests were conducted under same condition using SIPX as a collector, copper sulphate as the activator while varying the frother (17.5 g/t 1,1,1 triethoxy butane and 30 g/t MIBC (Methyl isobutyl carbinol)). The agitation intensity, the pulp level, pH, reagent dosages, and solid concentration were controlled during the course of the experiments. The grade and recovery obtained by Triethoxy butane is better in case of Zinc compared to MIBC. Similar trend is observed in Lead except grade.

| Frothers | Products | Weight, % | Grade % Pb | Recovery % Pb | Grade % Zn | Recovery % Zn |
|---|---|---|---|---|---|---|
| MIBC | Float | 10.44 | 6.94 | 84.89 | 14.935 | 75.79 |
| | Non float | 88.95 | 0.15 | 15.11 | 0.56 | 24.21 |
| Tri-ethoxy butane | Float | 13.51 | 5.8 | 87.45 | 16.20 | 83.84 |
| | Non float | 86.5 | 0.13 | 12.55 | 0.48 | 16.15 |

Coal

Coal was ground to size below 0.5 mm and used for all the flotation tests. Flotation studies were carried out in conventional Denver D12 sub-aeration flotation machine. About 400 grams of ore was mixed with 600 ml of water and reagent (triethoxy butane or diesel) was added and conditioned for 5 minutes. Air was released and flotation was carried out. The cell rpm of 1500 and percent solid of 10% was maintained during the flotation studies. All the flotation products were dried and analysed for ash. Yield of clean coal was taken parameters for performance evaluation of flotation

| Results | |
|---|---|
| Frother Type | Yield % at 15% Ash |
| Diesel | 27 |
| Triethoxybutane | 33 |

Example 2

Process for Preparing 1,1 Dimethoxy,2,4-Hexadiene 96 gms of 2, 4 Hexadienal was taken in a 2.0 ltrs capacity round bottom flask. Simultaneously 7 gms of Hydrochloric acid was dissolved in 160 gms methanol. The mixture of hydrochloric acid and methyl alcohol was added to 2,4 Hexadienal. The mass was heated slowly at a temperature of 70 deg C. for 9 hours. After 9 Hrs, the mass was cooled and neutralized by adding 6 gms of sodium carbonate under stirring. The mass was heated slowly at 70 deg for methyl alcohol recovery at atmospheric pressure by using 1.0 mtr glass column having condenser with chilled water circulation to avoid the loss of methyl alcohol to obtain 1,1 dimethoxy,2,4-hexadiene and polymer. After recovering methyl alcohol, the mass was cooled and filtered to remove sodium chloride and obtain 1,1 dimethoxy,2,4-hexadiene. 106 gms of 1,1 dimethoxy,2,4-hexadiene was obtained. The flash point of 1,1 dimethoxy,2,4-hexadiene was 68° C.

Example 3

Process for Preparing 1,1 Diethoxy 2,4,6 Octatriene 122 gms of 2,4,6 octatrinal was taken in a 1.0 ltr capacity round bottom flask along with reflux condensor. Simultaneously 5 gms of para toluene sulphonic acid was dissolved in 920 gms of ethyl alcohol. The mixture of ethyl alcohol and para toluene sulphonic acid was added to 2,4,6 octatrinal. The mass was heated slowly at 80° C. for 9 hrs. After reaction the mass was cooled and neutralized by adding 8 gms of sodium carbonate under stirring. The mass was heated slowly at 78° C. for recovering ethyl alcohol at atmospheric pressure by using 1.0 Mtr Glass column having condenser with chilled water circulation to avoid the loss of ethyl alcohol and to obtain 1,1 diethoxy 2,4,6 Octatriene and polymer. After recovering ethyl alcohol, the reaction mass was cooled and filtered to remove sodium salt of paratoluene sulphonic acid and obtain 1,1 diethoxy 2,4,6 Octatriene. 150 gms of 1,1 diethoxy 2,4,6 Octatriene was obtained. The flash point of 1,1 diethoxy 2,4,6 Octatriene was 70° C.

Example 4

Process for Preparing Low Flash Point 1,1,1 Triethoxy Butane 70 gms of crotonaldehyde, 920 gms of ethyl alcohol was charged in to a round bottom flask, which was attached to a reflux condensor. 10 gms of paratoulene sulphonic acid was added to the round bottom flask and the contents were heated at a temperature of 60° C. for 5 hours. After heating, the reaction mass was cooled and was neutralized by adding 4 gms of sodium carbonate at room temperature. The reaction mass was distilled at under vaccum to recover partially ethyl alcohol. The partially recovered ethyl alcohol along with unreacted crotonaldehyde was recycled back to the round bottom flask containing crotonaldehyde, ethyl alcohol and para toluene sulphonic acid. The remaining product obtained was 130 gms of 1,1,1 triethoxy butane having flash point of 48 deg C.

Thus, as can be seen from a comparison of examples 1 and example 4, maintaining a low temperature for the reaction resulted in 1, 1, 1 triethoxy butane having low flash point of 48° C., which is difficult to handle.

The invention claimed is:

1. A process for preparing a high flash point frothing agent having a flash point above 60° C., the process comprising:
   treating an aldehyde with an alcohol in the presence of an acid catalyst at a temperature of 75° C. to 80° C. to form a mixture; and
   adding a carbonate salt to the mixture for neutralizing the acid catalyst and to obtain frothing agent and polymer.

2. The process as claimed in claim 1, comprising heating the mixture for 3 to 4 hours after adding carbonate salt.

3. The process as claimed in claim 1 comprising distilling the mixture to remove unreacted alcohol and optionally recycling the unreacted alcohol to the step of treating aldehyde with an alcohol in the presence of an acid catalyst.

4. The process as claimed in claim 1 comprising distilling the mixture to obtain pure frothing agent.

5. The process as claimed in claim 4, wherein the pure frothing agent is obtained by fractional distillation.

6. The process as claimed in claim 1, wherein the aldehyde is an α-β unsaturated aldehyde having $C_4$-$C_{10}$ carbon atoms selected from crotonaldehyde, 2-ethyl hexenal, 2-ethyl crotonaldehyde, 2, 4-hexadienal, 2,4,6-octatrinal or mixture thereof.

7. The process as claimed in claim 1, wherein the alcohol is an aliphatic alcohol having $C_3$ to $C_{10}$ carbon atoms selected from methyl alcohol, ethyl alcohol, propyl alcohol, butyl alcohol, hexanol, octanol or mixture thereof.

8. The process as claimed in claim 1, wherein the carbonate salt is selected from sodium carbonate, calcium carbonate, magnesium carbonate or mixture thereof.

9. The process as claimed in claim 1, wherein the acid catalyst is selected from hydrochloric acid, sulfuric acid, paratoluene sulphonic acid, Indion-130 or mixture thereof.

10. The process as claimed in claim 1, wherein the purity of the high flash point frothing agent is 92-95%.

* * * * *